United States Patent [19]

Kobayashi

[11] Patent Number: 4,868,645

[45] Date of Patent: Sep. 19, 1989

[54] LIGHT CONTROL DEVICE FOR ENDOSCOPE

[75] Inventor: Kazunari Kobayashi, Hachioji, Japan

[73] Assignee: Olympus Optical Co., Ltd., Tokyo, Japan

[21] Appl. No.: 200,152

[22] Filed: May 26, 1988

[30] Foreign Application Priority Data

May 27, 1987 [JP] Japan .................... 62-130360

[51] Int. Cl.$^4$ .................... A61B 1/04; A61B 1/06
[52] U.S. Cl. .................... 358/98; 128/6; 358/213.16
[58] Field of Search ............ 358/98, 168, 174, 213.16; 128/6

[56] References Cited

U.S. PATENT DOCUMENTS

| 4,535,758 | 8/1985 | Longacre | 358/98 |
| 4,593,313 | 6/1986 | Nagasaki | 358/98 |
| 4,628,362 | 12/1986 | Waehner | 358/168 |

*Primary Examiner*—Howard W. Britton
*Attorney, Agent, or Firm*—Armstrong, Nikaido, Marmelstein, Kubovcik & Murray

[57] ABSTRACT

A video converter can be mounted on an optical endoscope which has an image guide capable of transmitting an optical image formed by an objective optical system. The video converter incorporates a solid-state imaging device having a plurality of pixels. The levels of the outputs from the pixels of the solid-state imaging device are compared with a dark current level, and the size of the imaging area of the image guide is detected from the result of the comparison. A photo-sensing/imaging area scaling signal is selected or generated in accordance with the result of detection if the imaging area of the image guide, and the intensity of the illuminating light is controlled in accordance with the actual imaging area which is determined by incorporating the photo-sensing/imaging area scaling signal.

15 Claims, 9 Drawing Sheets

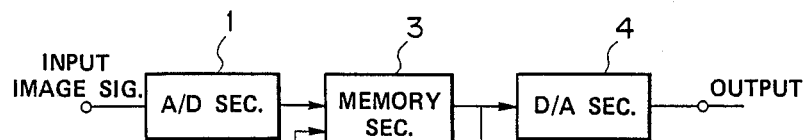
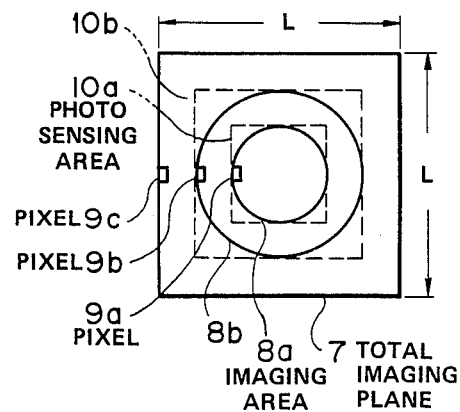
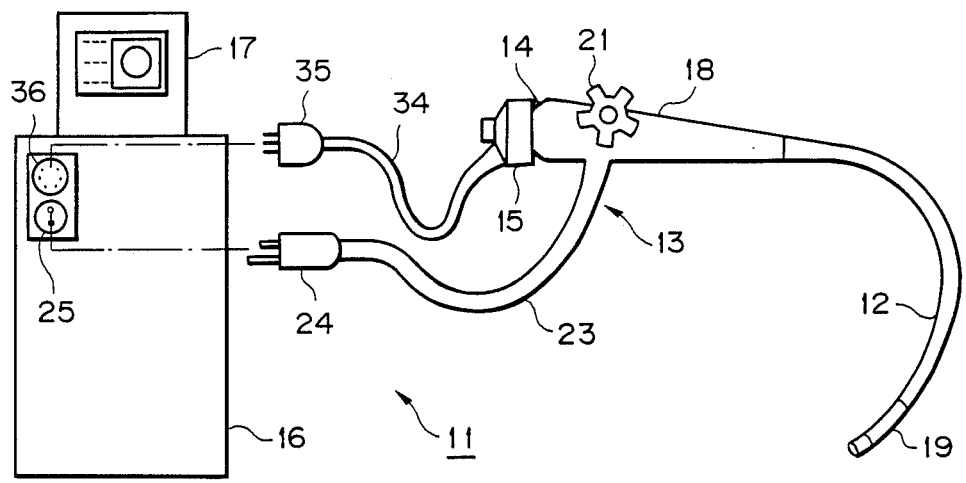

FIG. 6
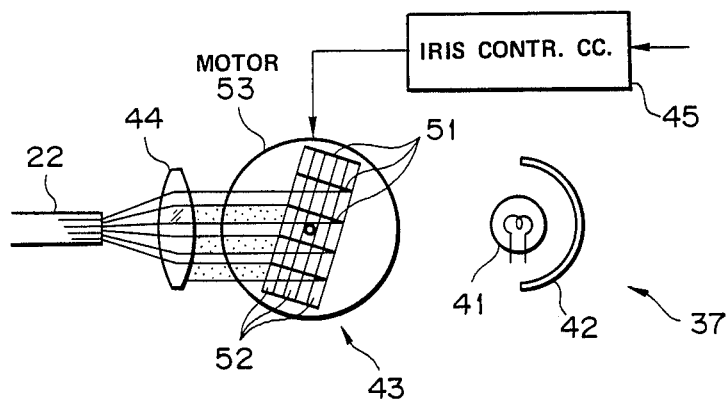
FIG. 8
FIG. 9
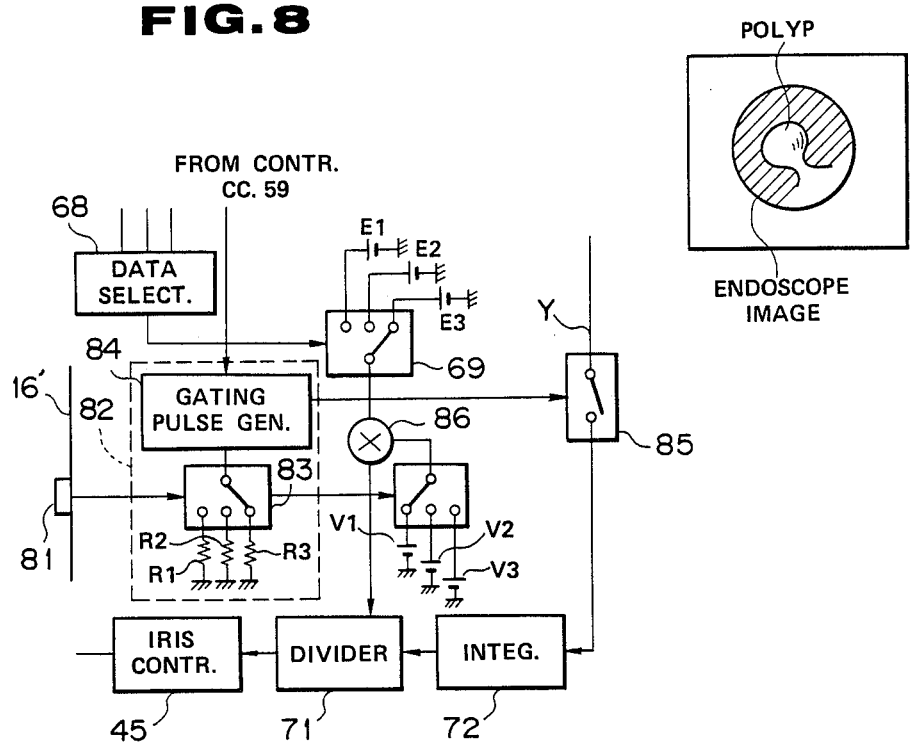

LIGHT CONTROL DEVICE FOR ENDOSCOPE

BACKGROUND OF THE INVENTION

Field of the Invention and Description of Related Arts

The present invention broadly relates to an optical endoscope and, more particularly, to a light control device for an endoscope capable of automatically maintaining an adequate level of light intensity regardless of the size of the image frame.

In recent years, endoscopes find spreading use because it enables an affected part of a living body to be observed by an elongated probe or sensing portion which is adapted to be inserted into a body cavity, thus eliminating any surgical operation for cutting out the affected part.

In recent years, soft endoscopes, known also as fiber scopes, have been proposed in which an image guide is constituted by a flexible fiber bundle for easy insertion into curved body cavities.

Fiber scopes of various diameters are available and selectively used according to the objective portions. Therefore, when a video converter is connected to the fiber scope to enable monitoring, the size of the image, i.e., the diameter of the endoscopic image on the monitor, varies depending on the diameter of the fiber scope to which the video converter is connected.

In addition, the level of the light control also is changed according to the diameter of the image guide constituted by the fiber scope.

Since the light intensity level varies according to the diameter of the image guide of the fiber scope bundle, it is necessary to manipulate, for example, a light control switch, in order to set the light intensity at the optimum level. Thus, the light control adjusting operation has to be conducted each time the scopes of different image frame size is used. This is quite troublesome and, if the endoscopic observation has been started without previous adjustment, it is necessary to conduct the adjustment in the course of the inspection, with the result that the inspection is suspended or the inspection time is prolonged, thus adversely affecting the inspection.

Under this circumstance, the specification of the U.S. Pat. No. 4,628,362 discloses an endoscope apparatus in which a window is defined in an image area and the brightness of the monitor image is automatically controlled in accordance with a signal derived from the window.

This known apparatus, however, requires a manual setting when the image guide is changed to one having a different diameter. Thus, the above-described problems still remains unsolved.

OBJECTS AND SUMMARY OF THE INVENTION

Accordingly, an object of the present invention is to provide a light control device for an endoscope which can set the level of the light intensity at an optimum level even when the diameter of the image guide is changed.

Another object of the present invention is to provide a light control device for an endoscope which can set the illumination at the level optimum for the endoscopic observation of the objective affected part.

According to the present invention, a determination is made as to whether the levels of signals from a plurality of pixels of a solid-state imaging device exceed a dark current level. Then, the photo-sensing area corresponding to the actual imaging area of the imaging device corresponding to the area of the image guide is detected in accordance with the result of the above-mentioned determination. Subsequently, a light control signal is generated by selecting/generating a correction signal corresponding to the actual photo-sensing area, whereby the light is controlled and optimized for image guides having different areas.

BRIEF DESCRIPTION OF THE DRAWINGS

FIG. 1 is a block diagram of an essential portion of the light control device according to a first embodiment;

FIG. 2 is an illustration showing the imaging surface of a solid-state imaging device;

FIG. 4 is an illustration of the whole system of the first embodiment;

FIG. 6 is an illustration of a light source device;

FIG. 8 is an illustration of an essential portion of a second embodiment of the present invention;

FIG. 9 is an illustration of an image frame on an endoscope which has picked-up an image of a polyp;

DETAILED DESCRIPTION OF THE PREFERRED EMBODIMENTS

Figure 3:
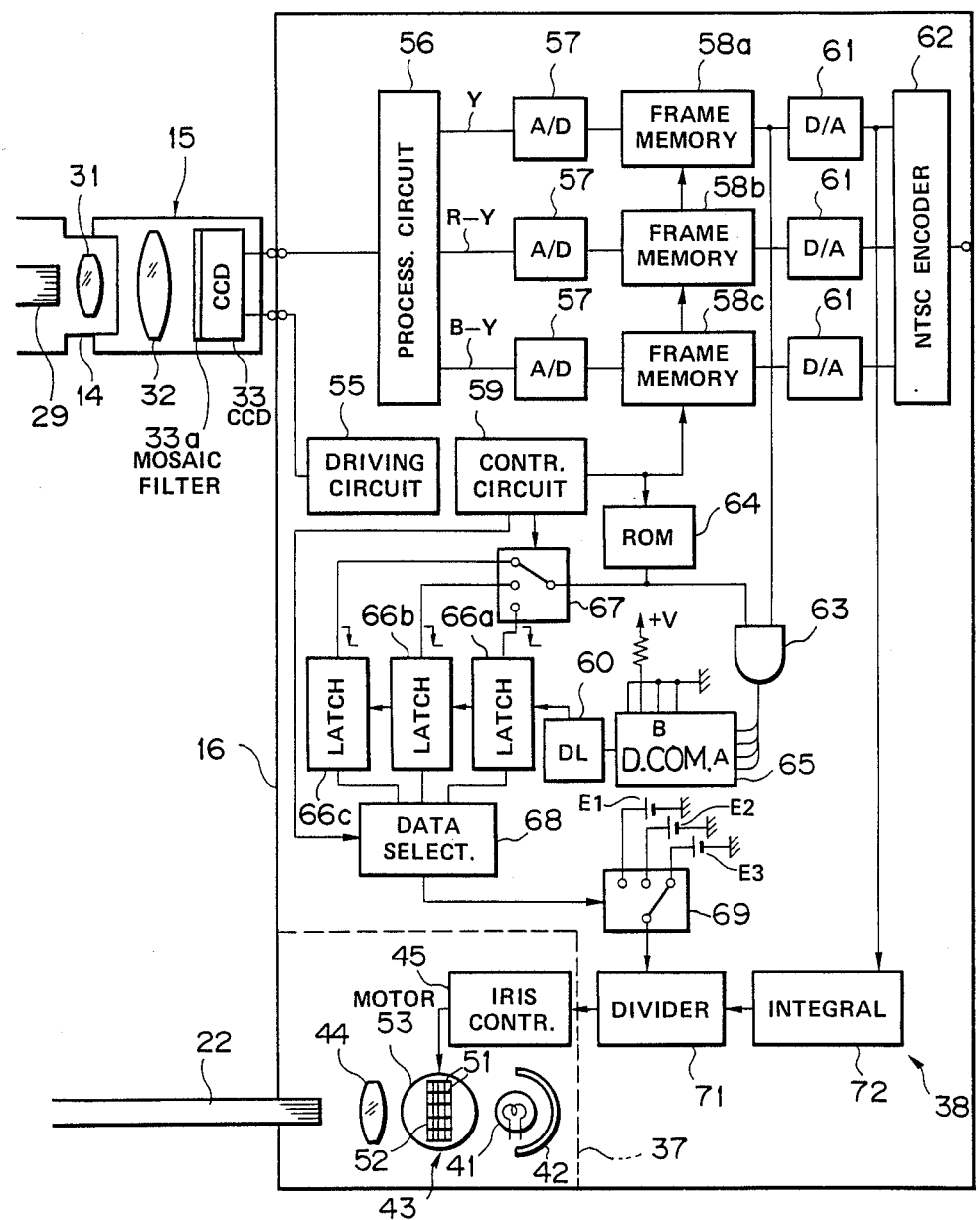
FIG. 3 is a block diagram of a first embodiment.
Figure 5:
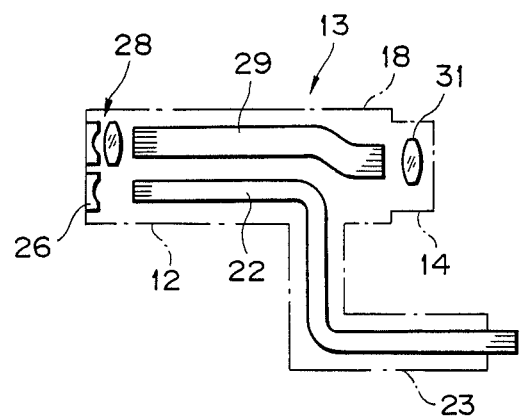
FIG. 5 is an outline of the structure of a fiber scope.

Before commencing the detailed description of the preferred embodiments, a description will be made first as to the principle of the present invention.

Referring to FIG. 1 which is a block diagram illustrating the principle of the present invention, an optical image transmitted through an image guide is photoelectrically converted by a solid-state imaging device of a video converter so as to become an image (video) signal. The thus obtained image (video) signal is input to an analog-to-digital converter 1 so as to be converted into digital signals. The digital signals are stored in predetermined addresses of a memory 3 by an address setting device 2. When the video data corresponding to one image frame has been stored, the video data thus stored is read and input to a digital-to-analog converter 4 so as to be output therefrom as analog video signal. At the same time, the data of the memory 3 is input to a digital comparator 5 which conducts a determination as to whether the output level of the memory 3 is above a predetermined level or not, and the result of the comparison is input to a photo-sensing area switching circuit 6.

The photo-sensing area switching circuit is adapted to conduct switching of scaling of the photo-sensing area which is actually used when the light quantity from the light source is controlled in accordance with the output from the solid-state imaging device, so as to set a photosensing condition corresponding to the diameter (area) of the selected image guide, whereby light control is conducted optionally even when an image guide of a different diameter is used.

Referring to FIG. 2, it is assumed here that the whole imaging surface 7 of a solid state imaging device has a size of L×L, while the image area of the fiber scope (image guide) has a size as denoted by 8a. In this case, pixels 9b and 9c cannot receive light, although pixels 9a can receive light. Meanwhile, output signals are sequentially output from the memory 3 in the order of address set by the address setting device 2, including the outputs from the pixels 9a, 9b and 9c. As the digital comparator 5 is informed of the fact that outputs have been derived from the pixels 9a, 9b and 9c, the digital comparator 5 compares the output values from the pixels 9a, 9b and 9c with a reference level, and conducts a determination as to whether the levels of these outputs are above a predetermined level or not.

The levels of the outputs from the pixels 9b and 9c correspond to the dark current level which is substantially equal to the level of a slight noise. Therefore, if the reference level is set to be higher than the level of the greatest noise component, the levels of the outputs from the pixels 9b and 9c are below the reference level. On the other hand, the level of the output from the pixels 9a exceed this reference level.

The result of the comparison is delivered to the photosensing area switching circuit 6 so that the control of the light output, i.e., the light control, is effected in accordance with the output signals derived from the photosensing area 10a corresponding to the image area size 8a of the fiber scope.

Similarly, when the image area of the fiber scope to which the video converter is connected has a size as denoted by 8b, the actual photo-sensing area is the square area 10b. When the whole image area of the solid-state image pickup device consttutes the image area size of the fiber scope, a light control signal is generated to control the light output of the illuminating light by using the entire imaging surface as the photosensing area.

Thus, even when a fiber scope having an image having a different image area size is used, the light is controlled optimumly to eliminate any influence of the change in the image area size of the fiber scope, by virtue of the fact that the light control is effected through a scaling correction corresponding to the actual photo-sensing area corresponding to the image area size.

A first embodiment of the present invention will be described in detail hereinafter with specific reference to FIGS. 3 to 7.

Referring to FIG. 4, an endoscope apparatus 1 incorporating a light control device of the first embodiment of the invention has an endoscope (fiber scope) 13 having an insertable portion 12 which can be inserted into body cavities, a video converter 15 adapted to be attached to the eye-contact portion 14 of the fiber scope 13 and capable of producing photo-electrically converted image signal, a video signal processing unit 16 incorporating a light source means, and a monitor 17 having a display for displaying the video signal output from the processing unit 16.

The fiber scope 13 has a manipulating portion formed at a portion thereof near the proximal end of the insertable portion 12 and having a comparatively large diameter. The manipulating portion 18 has an angle knob for selectively bending a curved portion 19 near the distal end of the insertable portion 12. A light guide 22 (see FIG. 5) extended through the insertable portion 12 runs through a light guide cable 23 extended from the manipulating portion 18. A light-source connector plug 24 is provided on the end of the light guide cable 23. The connector plug 24 is adapted to be connected to the light source connector receptacle 25 of the video signal processing unit 16.

As the light source connector plug 24 is connected to the light source connector receptacle 25, the illumination light is introduced to the incident end surface of the light guide 22 and the thus introduced light is transmitted to be emitted from the emerging end of the light guide 22. The light is then diverged by a light distribution lens so as to be applied to an object.

The object illuminated by the light applied through the light distribution lens 26 reflects light which is focused at the focal plane of an objective lens which is provided on the end of the insertable portion 12 so as to form the image of the object on the end surface of an image guide 29 which is disposed at the focal plane of the objective lens 28. As is the case of the light guide 22, the image guide 29 is constituted by a fiber bundle and the optical image formed on the end surface of the image guide 29 is transmitted to the rear end surface of the eye-contact portion 14 so as to be observed by a naked eye through an eye-contact lens 31 disposed behind the rear end surface of the eye-contact portion.

As shown in FIG. 3, the video converter 15 which can be mounted on the eye-contact portion 14 of the fiber scope 13 has an image-forming lens 32, a CCD as the solid-state imaging device disposed at the position where the image is formed through the image forming lens 32, and a signal cable 34 (see FIG. 4) connected to the CCD 33. A signal connector plug 35 is provided on the end of the signal cable 34 so as to be connected to a signal connector receptacle 36 of the video signal processing unit 16. A mosaic filter 33a is provided in front of the imaging surface of the CCD 33 so as to effect color separation of the signal from each pixel into R, G and B colors.

As shown in FIG. 3, the video signal processing unit 16 has a light source unit 37 for supplying illumination light to the light guide 22 of the fiber scope 13, and a signal processing unit 38 for conducting processing on the image signal output from the CCD 33 of the video converter 15.

The light source unit 37 is composed of a lamp 41 capable of emitting white light, a concave mirror 42 reflecting the white light from the lamp 41 so as to form a parallel white light beam, an aperture device 43 disposed at an intermediate portion of the parallel beam and adapted for varying the quantity of light which passes therethrough, and a condenser lens 44 which condenses the light from the aperture device 43 onto the incident end surface of the light guide 22. The light control device is so designed that the quantity of the illuminating light is controlled optimally for the imaging by the CCD 33, through the control of the quantity of the light which passes through the aperture device 43.

As will be seen from FIG. 6, the aperture device 43 has a plurality of parallel plates 51, 51, . . . , 51 which are fixed at a predetermined interval by means of a fixing bars or plates 52, . . . , 52, and a motor 53 capable of swinging the parallel plates 51, . . . , 51 from the positions parallel to the optical axis to a maximum swinging angle of several tens of degree. The light quantity can be controlled by applying driving signal to the motor 53. FIG. 3 shows the state of the light control device in a state in which the quantity of the transmitted light is maximized, while, in FIG. 5, the motor 53 has operated through a predetermined angle so as to reduce the quantity of the transmitted light.

As shown in FIG. 3, the CCD 33 is adapted to be supplied with a CCD drive signal from a drive circuit 55 so as to enable the image signals to be read therefrom. The thus read image signal is input to a process circuit 56 of an imaging means having a mosaic filter, so that the process circuit 56 delivers a luminance signal Y and color difference signals R-Y and B-Y. These luminance signals Y and the color difference signals R-Y and B-Y are stored in the frame memories 58a, 58b and 59c through analog-to-digital converters 57. Thus, image data corresponding to one frame are stored in the frame memories 58a, 58b and 58c. The data are simultaneously read in accordance with the address signals output from the control circuit 59 and are input to an NTSC encoder 62 through digital-to-analog converters 61 and are converted into NTSC type composite video signal which is then output to the monitor.

The output signal from the frame memory 58a is input to AND circuits 63 having two inputs. The number of the AND circuits 63 correspond to the number of the conversion bits of the analog-to-digital converter 57. The AND gate 63 is opened in accordance with the level of the gate signal stored beforehand in a ROM 64 and read in accordance with the address signal from the control circuit 59. More specifically, the signal is passed through the AND circuit 63 and is applied to the input terminal A of the digital comparator 65 when the gate signal is "H".

The ROM 64 stores binary signals which takes the "H" level only when the addresses of the memory elements storing the signals received by the pixels 9a, 9b, 9c are applied and the "L" level in all other cases. Therefore, when digital signals are read from the frame memory 58a, the output of the ROM 64 is changed to "H" when the signals from the pixels 9a, 9b and 9c are read,so that the AND circuit 63 is opened to enable the digital data of the luminance signal Y of the frame memory 58 to be applied to the digital comparator 65 which maybe of the type disclosed in the U.S. patent application Ser. No. 7,485. A digital reference data (4-bit data in the illustrated embodiment) of a level slightly higher than the dark current level and slightly greater than the maximum noise level is beforehand preset on the input terminal B of the digital comparator 65. The input data is received by the input terminal A is compared with the reference value data preset on the input terminal B. The results of the comparison are applied to the data input terminals of latch circuits 66a, 66b and 66c through a delay element 60 and are latched by the latch circuits at the timing at which the output of the ROM 64 falls from the "H" level to the "L" level. More specifically, the signals corresponding to the pixels 9a, 9b and 9c are sequentially compared with the reference value through an analog switch 67 which conducts switching or change-over operation under the control of the control circuit 59, and the results of the comparison are latched by the latch circuits 66a, 66b and 66c. For instance, referring to FIG. 3, the analog switch 67 is set such that its contact c takes the on state and then takes an address value corresponding to the pixel 9c in the ROM 64. As a result, the AND circuit 63 is opened so that the light signal derived from the pixel 9c is input to the digital comparator 65. The signal is then compared with the reference value by the digital comparator and the result of the comparison is input through the delay element 60 to the latch circuits 66a, 66b and 66c. Subsequently, the next address value is taken so that the output of the ROM 64 is switched from "H" to "L" and is latched by the latch circuit 66c. The delay element 60 is provided for the purpose of ensuring that the result of the comparison is picked up correctly at the timing of latching, so that the amount of the delay posed by the delay element may be about half the period corresponding to one pixel.

Three values are thus latched in the latch circuits 66a, 66b and 66c. Then, the control circuit 59 operates to apply a strobo signal to a data selector 68 so that the comparison results stored in the three latch circuits 66a, 66b, 66c are converted to binary-coded switch control signal. The switch control signal is then input to the analog switch 69. The analog switch 69 selectively turns on the three values (voltage values) E1, E2, E3 which correspond to the photo-sensing periods corresponding to different photo-sensing areas. The selected voltage value, i.e., the scaling correction value corresponding to the photo-sensing area, is input to a divider 71 which operates to divide the output signal from an integration circuit 72 adapted for integrating the luminance signal Y so as to generate light control signal which is then input to the aperture control circuit 45.

The integration circuit 72 is designed to integrate the luminance signal Y through a period of for example, one frame. Actually, however, the period of output of the signal varies depending on the area of the image guide, so that the accuracy of the light control signal is impaired when the averaging is conducted with a single common frame period. In this embodiment, however, the actual imaging area is detected through the detection of the photo-sensing area, and the scaling correction of the photo-sensing area is effected by conducting the division by the voltage value EI (I=1, 2 or 3) which represents the imaging period of the detected imaging area, whereby the light control signal correctly corresponding to the image area can be obtained. The amount of operation of the motor 53 is so controlled in relation to the level of the light control signal such that the angle of rotation of the output shaft of the motor is increased as the level of the light control signal becomes higher, such as to reduce the quantity of the transmitted light thereby automatically attaining the illumination light intensity optimum for the imaging by the CCD 33.

Figure 7:
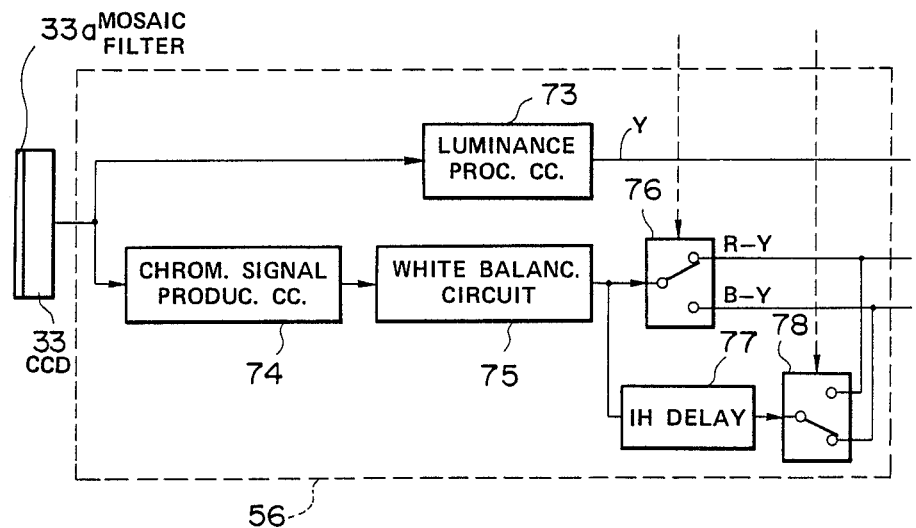
FIG. 7 is a block diagram of a process circuit.

The process circuit 56 described above is constructed, for example, as shown in FIG. 7.

The signal from the CCD 33 is formed into a luminance signal Y through a luminance signal processing circuit 73. The signal from the CCD 33 also is input to a color signal reproducing circuit 74 so that color difference signals R-Y and B-Y are generated time-sequentially for each horizontal line. At the same time, white balance correction is executed by a white balance circuit 75. The output from the white balance circuit 75 is directly input to an analog switch 76 and also to an analog switch 78 after a delay corresponding to the period of one horizontal line performed by an lH delay circuit 77, whereby color difference signals R-Y and B-Y are obtained in accordance with the switching signal from a timing generator which is not shown. In the first embodiment as described, imaging area detection pixels 9a, 9b, 9c are provided so as to correspond to difference sizes of the area of the image guides 22 of the fiber scope 13, so as to enable the light measurement to be conducted only in the actual imaging area, through a determination as to whether the signals (luminance components) from the pixels exceed predetermined threshold level which substantially correspond to the maximum noise level. It is therefore possible to automatically set the light intensity at a level optimum for the imaging operation of the imaging device, regardless of any change in the diameter or area of the image guide 22 of the fiber scope 13 on which the video converter 15 is mounted, whereby the object image is formed with an adequate level of contrast. Therefore, the operator is relieved from troublesome work which has been heretofore necessary for manually adjusting the level of illumination, and can obtain the image in good condition without fail.

FIG. 8 shows a critical portion of a second embodiment of the present invention. In this second embodiment, the photo-sensing area can be set to be smaller than the area of the image guide 22 of the fiber scope, in contrast to the first embodiment in which the photo-sensing area directly corresponds to the imaging area determined by the area of the image guide 22.

The second embodiment has a photo-sensing area selection button 81 disposed in front of the video signal processing circuit 16', for the purpose of enabling the user to select one from a normal mode which is the mode exactly the same as the first embodiment and two inner region photo-sensing modes which provide photo-sensing areas inside the area of the normal mode.

In operation, the user manipulates the analog switch of the photo-sensing area selection circuit 82 so as to appoint one from three resistors R1, R2 and R3 which have resistance values RI(I=1,1,3). As a result, the pulse width of a pulse generated by a gate pulse generator 84, which is constituted by a monostable multivibrator, e.g., a monostable multivibrator shown in Ser. No. 74,121 is changed according to the resistance value of the resistor appointed by the user.

The gate pulse generator 84 generates a pulse which takes a high level in the area which contains the center of the CCD imaging surface and which is symmetrical with respect to this center. The analog switch 85 is kept on only in the period in which this pulse takes the high level, so as to enable the luminance signal Y to be input to the integration circuit 71 via the D/A converter 61.

In this embodiment, the photo-sensing area is set within the actual imaging area. It is, therefore, necessary to conduct the normalization during the light measurement in the actual photo-sensing area. This can be accomplished, for example, by the use of the following arrangement. Namely, a multiplier 86 is provided between the analog switch 69 and the divider 71 so as to effect multiplication with a suitable multiplication factor in relation to the selecting operation performed through the selection button 81. A plurality of multiplication factors are generated in the forms of voltages V1, V2 and V3. According to this second embodiment, it is possible to set the optimum light level at the center of the endoscopic image, and the size of the photo-sensing area centered at the endoscopic image also can be selected freely.

When the object to be imaged is a projection such as a polyp, if the photo-sensing is conducted by averaging the brightness of the whole endoscopic image, a halation takes place in the region including the polyp while other portions are darkened to a level which cannot be observed materially. According to the second embodiment, however, the automatic light measurement is conducted in the region containing the polyp so that the state of the polyp can be observed with an adequate light intensity level, by selecting the mode in which the light measurement is conducted only in the central region.

According to this second embodiment, if the object portion to be observed is set at the center, the illumination level is automatically optimized for the observation of this portion, even when the portion is a part of the imaging area.

Figure 10:
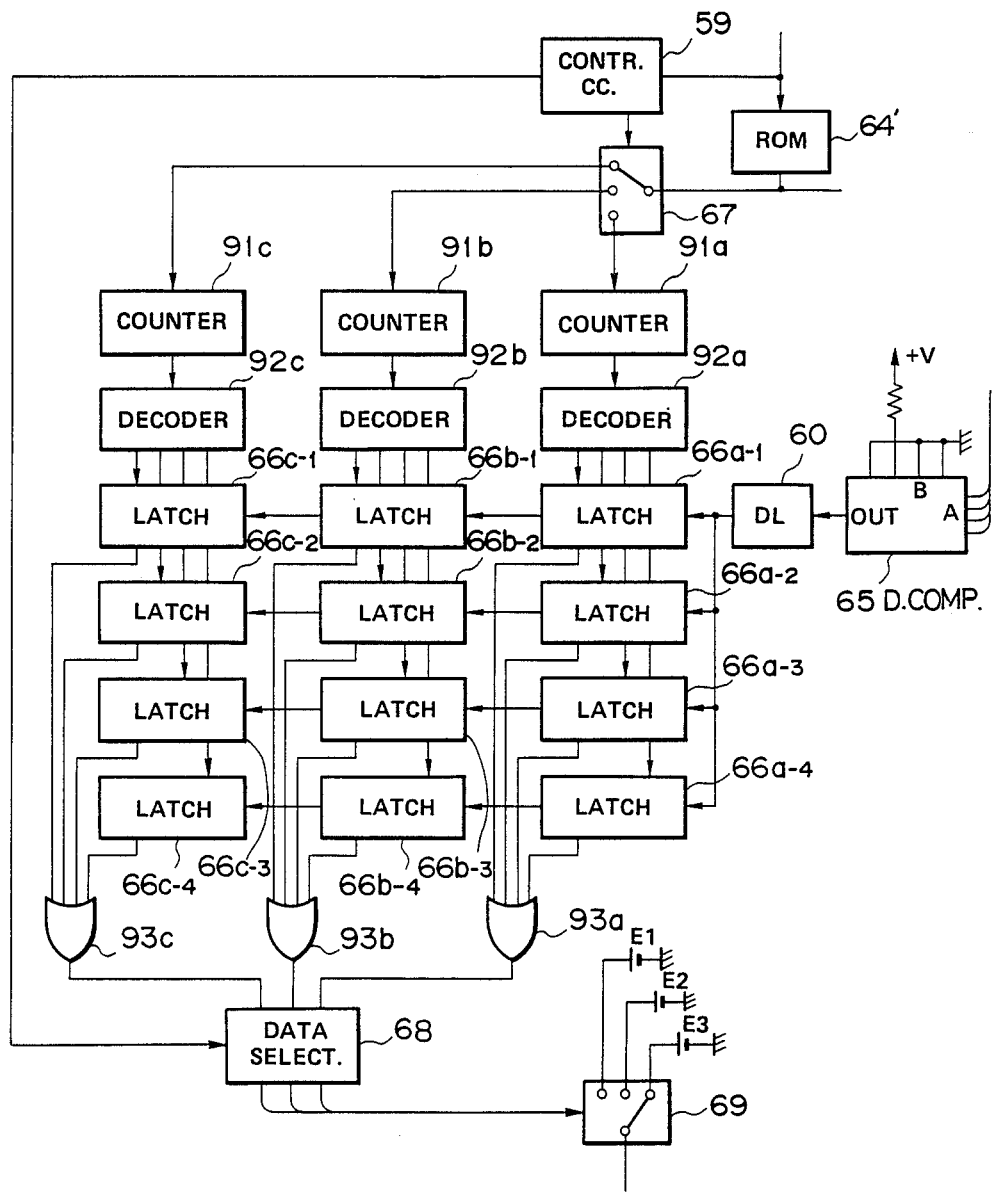
FIG. 10 is a block diagram of an essential portion of a third embodiment of the present invention.

FIG. 10 shows an essential portion of a third embodiment of the present invention.

Figure 11:
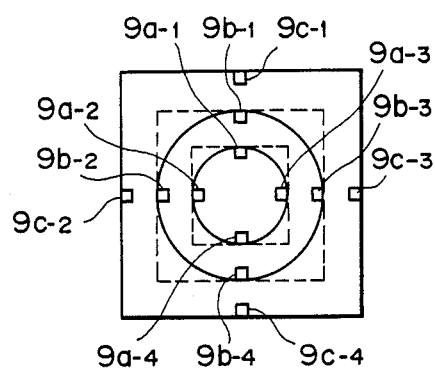
FIG. 11 is an illustration of pixels employed for the purpose of detection of the photo-sensing area in the third embodiment.

In the first embodiment described before, each of the photo-sensing areas 10a, 10b and 10c is detected from the output from a single pixel 9a, 9b or 9c. In contrast, the third embodiment employs a plurality of pixels, e.g., four pixels, for the detection of each photo-sensing area, as shown in FIG. 11. These pixels are denoted by $9_{i-1}$, $9_{i-2}$, $9_{i-3}$, $9_{i-4}$ (i=a,b,c). In this embodiment, a determination is conducted as to whether the greatest one of the signals derived from these pixels exceeds a reference level which is set to be higher than the dark current level, and the result of the determination is used for the purpose of switching of the photo-sensing area as in the first embodiment. Therefore, in the signal processing unit 38 shown in FIG. 3, there are four latch circuits $66_{i-1}$, $66_{i-2}$, $66_{i-3}$, $66_{i-4}$ for receiving the output from the digital comparator 65 through the delay element 60 so as to store the results of the comparison between the signals from the respect pixels $9_{i-1}$, $9_{i-2}$, $9_{i-3}$, $9_{i-4}$ (i=a,b,c). The output from the analog switch 67 is delivered to the latch enable terminals of the respective latch circuits $66_{i-1}$, $66_{i-2}$, $66_{i-3}$, $66_{i-4}$ through four-noted counters $91_i$ and decoders $72_i$, whereby the four types of comparison result are sequentially latched.

The outputs from the four latch circuits $66_{i-1}$, $66_{i-2}$, $66_{i-3}$, $66_{i-4}$ are delivered through the respective OR circuits having four inputs to the data selector 86. Thus, four comparison results are made to pass through the OR circuit $93_i$ so that a determination is conducted as to whether one or more of the four light measurement signals exeed the reference level, and the switching of the light measurement area is conducted in accordance with the result of this determination. The ROM 64' is designed to output a signal of "H" level at the address value corresponding to each of the pixels $9_{i-1}$, $9_{i-2}$, $9_{i-3}$, $9_{i-4}$. The arrangement may be such that the switching signal is produced in accordance with the result of determination as to whether the mean value of the outputs from the pixels $9_{i-1}$, $9_{i-2}$, $9_{i-3}$, $9_{i-4}$ exceeds a predetermined level. It is also possible to arrange such that the switching signal is produced on the basis of the majority level of the signals representing the comparison results.

Figure 13:
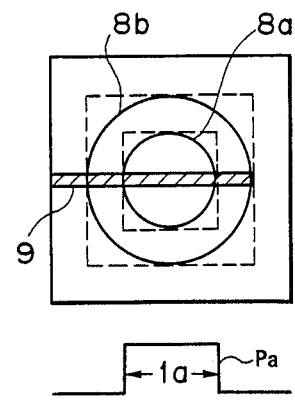
FIG. 13 is an illustration of pixels employed for the purpose of detection of the photo-sensing area in the fourth embodiment of the present invention.
Figure 12:
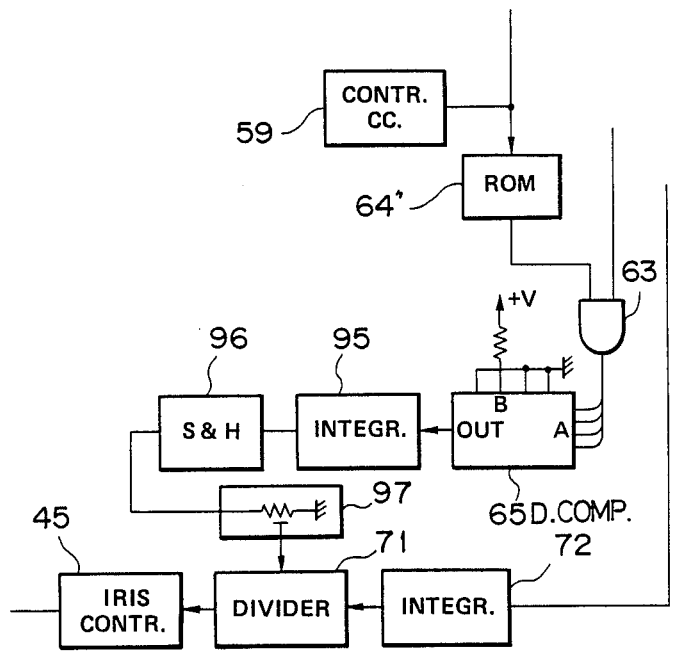
FIG. 12 is a block diagram of an essential portion of a fourth embodiment of the present invention.

FIG. 12 shows a fourth embodiment of the present invention in which, as shown in FIG. 13, the photo-sensing area is determined in accordance with the evaluation of the output signals from all the pixels in a central horizontal line. The construction of the fourth embodiment is materially the same as that shown in FIG. 3, except the following points. Namely, in this embodiment, the output from the digital comparator 65 is delivered through an integration device 95 to a sample hold circuit 96 so as to be held in the latter, and the voltage value thus sample-held is supplied to the divider 71 through a coefficient device 97. Then, the aperture control circuit 45 is controlled in accordance with the output from the divider 71, thereby effecting the light control. In this embodiment, a ROM 64'' stores data which provides the output level "H" for all the addreses corresponding to the pixels 9 of FIG. 13 which are used in the light measurement and the output level "L" for all other addresses. In this embodiment, when the image area size of the fiber scope mounting the video converter is as that denoted by 8a, a pulse Pa of a pulse width 1a corresponding to the image area size 8a is output from the digital comparator 65 as shown in FIG. 13, and the value output from the digital comparator 65 is integrated by the integration device 95 and is sample-held by a subsequent sample hold circuit 96. Although in FIG. 13 the pixels used in the light measurement are arrayed in a horizontal row, it will be clear to those skilled in the art that the pixels may be arrayed in a vertical row. The integrated value which has been sample-held by the sample hold circuit 96 is proportional to the size of the light measuring area, and is input to the divider 71 through a coefficient device 97. In this embodiment, the a photo-sensing area scaling correction signal, which corresponds to the photo-sensing area, is automatically generated through integration of the signal which has passed through the digital comparator 65. It is therefore not necessary to provide any specific means which would provide correction signals corresponding to different image guide areas, e.g., the voltage values E1, E2 and E3 employed in the first embodiment. Thus, the fourth embodiment can be applied to a variety of image guide areas. The arrangement also may be such that the coefficient device 97 mentioned before is provided on the input side of the sample hold circuit 96. It is also to be understood that the provision of the coefficient device 97 is not essential.

Figure 14:
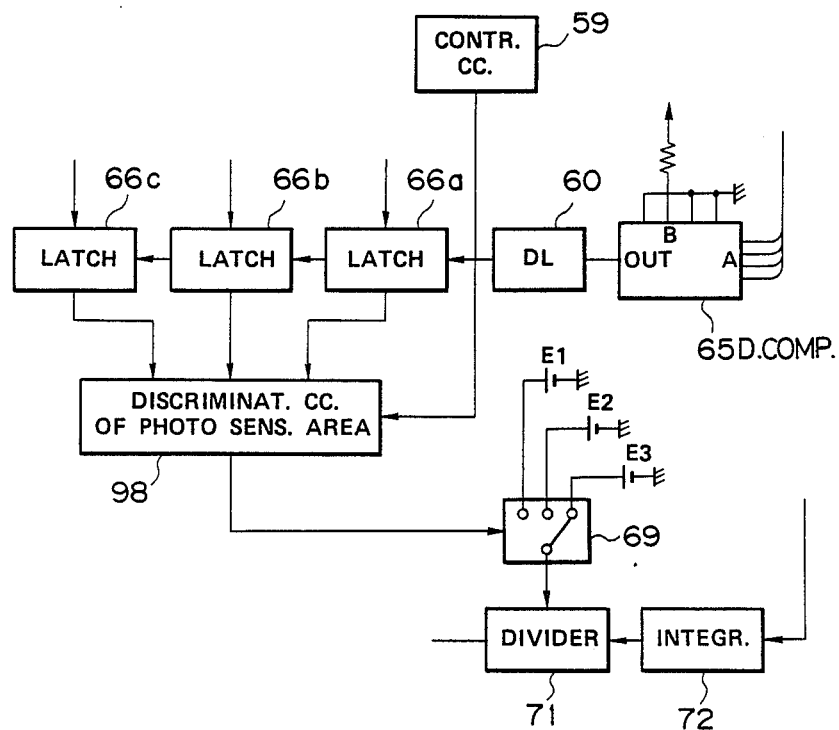
FIG. 14 is a block diagram of an essential portion of a fifth embodiment of the present invention.

FIG. 14 shows an esential portion of a fifth embodiment of the present invention. This embodiment is similar to the first embodiment but is different therefrom in that the outputs from three latch circuits 66a, 66b and 66c are input to a photo-sensing area judging circuit 98 which provides a switching signal for irreversibly switching the light mesuring area.

The latch circuits 66a, 66b and 66c are adapted for holding the data of "H" level only when the levels of the of the signals from the corresponding pixels 9a, 9b and 9c are higher than a predetermined level. In consequence, the light mesuring area judging circuit 98 operates in a sequence which will be explained hereinunder with reference to FIG. 15.

A comparison is conducted between data 66a, 66b, 66c latched by the respective latch circuits 66a, 66b, 66c for every n frames (n being an integer), thereby determining the photo-sensing area, and the switching of the analog switch 69 is conducted in accordance with the result of the determination. This photo-sensing area judging circuit 98 incorporates a data selector.

Figure 15:
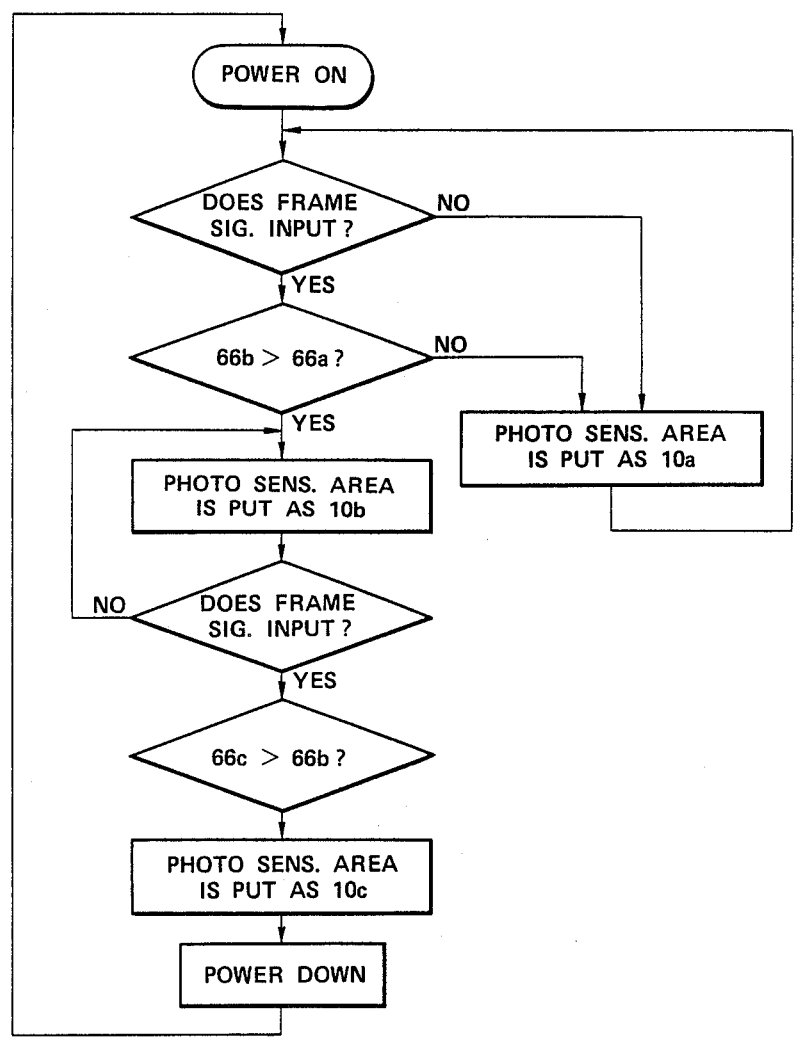
FIG. 15 is a flow chart showing the process for detecting the photo-sensing area in a fifth embodiment of the present invention.

The algorithm shown in FIG. 15 enables the photo-sensing area to be switched from the inner one to the outer ones, but does not allow the same to be switched from the outer one to the inner ones. Thus, the algorithm shown in FIG. 1 has a irreversible or unidirectional switching characteristic. When this switching is conducted, the state is switched from POWER ON to POWER DOWN and this state is continued until the initial setting is conducted.

The arrangement according to the fifth embodiment makes it possible to easily set the photo-sensing area optimumly for different fiber scopes having different imaging area sizes. It is to be pointed out that the light does not always uniformly impinge upon the scope or the image area. Namely, in some cases, only a portion of the image area is irradiated with a light component of a high intensity, while other portions does not materially receive light. The fifth embodiment does not require the photo-sensing area to be switched even in such a case. Thus, in the fifth embodiment, the outermost one of the pixels in receipt of the light determines the photo-sensing area and the switching into inner photo-sensing area is prohibited, whereby the photo-sensing is effecte in the area optimum for the image area size of the scope which is being used.

It will be clear to those skilled in the art that, although in the described embodiments three image guide sizes are available, this is only illustrative and the invention can be embodied with two or four or more fiber scopes having different imaging area sizes. It is also to be noted that the image guide may be constituted by a device other than the described fiber bundles. For instance, the image guide can be constituted by a relay optical system having a plurality of lensed arranged in series, as in the case of a hard or rigid endoscope system.

The use of the white light also is illustrative. For instance, it is possible to irradiate the object with light from different wavelength regions, e.g., red, green and blue, while constructing the solid-state imaging device with a surface sequence type color imaging device which does not have a mosaic filter.

Figure 16:
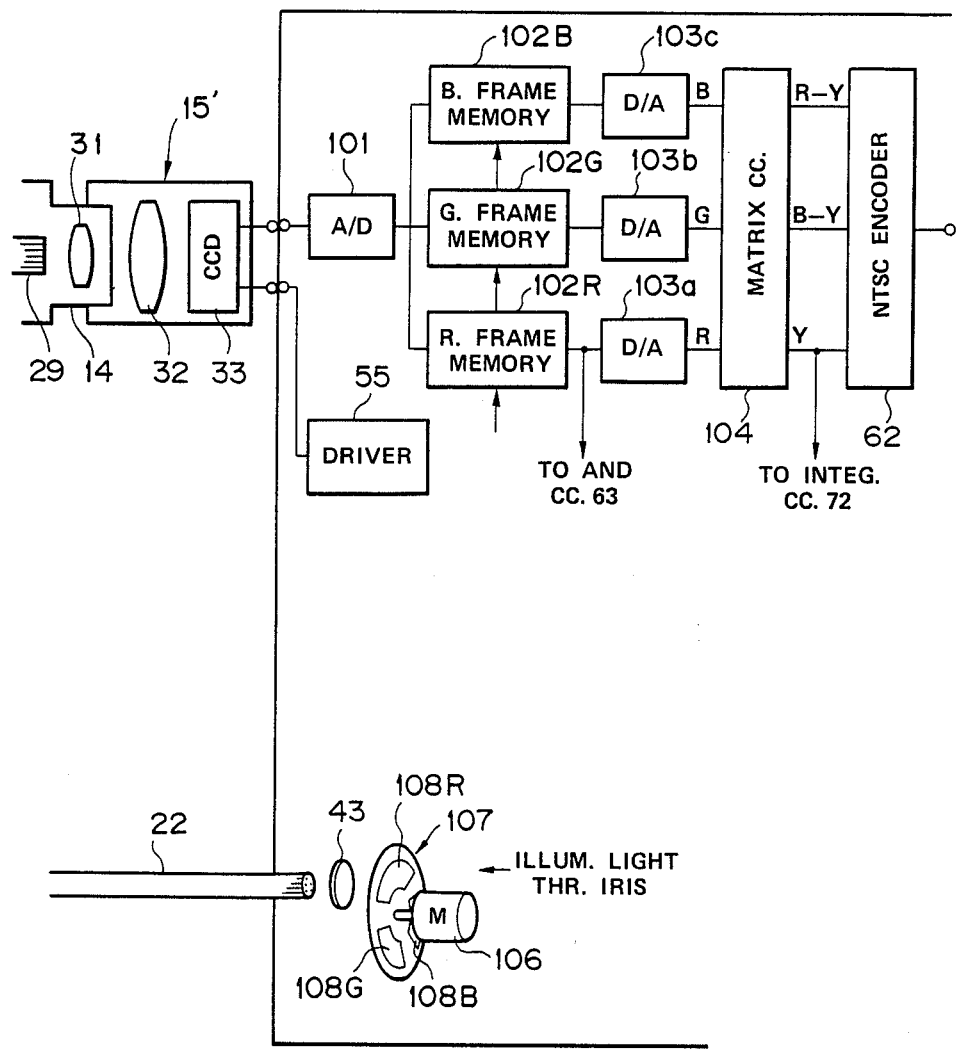
FIG. 16 is an illustration of a surface-sequence type light source device and imaging means.

FIG. 16 shows an essential portion of such an arrangement. In this embodiment, a video converter 15' incorporating a CCD 33 which does not have any mosaic filter is used in place of the video converter 15 of FIG. 3 which has a mosaic filter 33a. The output from the CCD 33 is input to R, G and B frame memories 102R, 102G and 102B through the A/D converter 101. Thus, the output from the R frame memory 102R for instance is input to the AND circuit 63. The outputs from the R, G and B frame memories 102R, 102G and 102B are supplied through digital-to-analog converters 103a, 103b and 103c to a matrix circuit 104, whereby the luminance signal Y and color difference signals R-Y and B-Y are generated. As in the case of the first embodiment, the output of the matrix circuit are input to an NTSC encoder 62, while the luminance signal Y is input to the integration circuit 72.

The light source unit 105 used in this embodiment is similar to the light source unit 37 shown in FIG. 3, except that a rotary color filter 107 adapted to be driven by a motor 106 is disposed between the aperture 43 and the lens 44. The rotary color filter 107 has a disk-like form with three sector-shaped openings which are equidistantly spaced in the circumferential direction. Color transmitting filters 108R, 108G and 108B capable of transmitting the light of red, green and blue wavelength regions are provided in these sector-shaped openings. Illumination light of red, green and blue are sequentially applied to the light incident end of the light guide 22 through this rotary color filter 107. Other portions are materially the same as those in the first embodiment.

Although the invention has been described through specific forms, it is to be understood that the described embodiments are only illustrative and the invention can be carried out in various other forms through, for example, partial combinations of the described embodiments. Thus, the described embodiemnts are not exclusive and various changes and modifications may be imparted thereto without departing from the scope of the invention which is limited solely by the appended claims.

What is claimed is:

1. An endoscope apparatus comprising:
    an endoscope including
        an elongated insertable portion,
        a light guide extended through said elongated insertable portion and transmitting illuminating light,
        an objective optical system attached to a distal end of said insertable portion and forming an image of an object,
        an image guide extended through said insertable portion and having an incident end surface at a focal plane of said objective optical system, said image guide transmitting an optical image, and
        an eye-contact portion opposing a light emitting end of said image guide;
    a video converter mounted on said eye-contact portion, said video converter including
        an image forming optical system forming the optical image transmitted through said image guide, and
        a solid-state imaging device disposed at a position where said optical image is formed by said image forming optical system;
    a signal processing means for processing output signals from said solid-state imaging device to form a video signal;
    display means for displaying an object image by the video signal output from said signal processing means;
    a light source unit supplying illuminating light to said light guide; and
    a light control device including
        level judging means for determining whether output signals, from a plurality of pixels on said solid-state imaging device, exceed a predetermined level,
        correction signal generating means for generating, in accordance with an output signal from said level judging means, a photo-sensing area correction signal corresponding to an actual imaging area on said solid-state imaging device on which an end area of said image guide is actually formed, and
        light control signal generating means for generating a light control means for controlling the illuminating light output from said light source unit by dividing the output signals from said solid-state imaging device by said correction signal.

2. A light control device for use in an endoscope apparatus which has an elongated insertable portion, a light guide extended through said insertable portion and transmitting illuminating light, an image guide extended through said insertable portion and transmitting an optical image, and a video converter mounted on an eye-contact portion of said image guide and incorporating a solid-state imaging device, said light control device comprising:
    level judging means for conducting a determination as to whether photo-electrically converted outputs from a plurality of pixels of said solid-state imaging device exceeds a predetermined level or not;
    correction signals generating means for generating, in accordance with an output from said level judging means, a photo-sensing area connection signal which corresponds to an actual imaging area on said solid-state imaging device on which an image is formed by light from a light emitting end of said image guide; and
    light control signal generating means for generating a light control signal for controlling a light output level of a light source unit which supplies illumination light to said light guide, by dividing an output from said solid-state imaging device by said correction signal.

3. An apparatus or device according to claim 1 or 2, wherein said video converter includes a color filter in front of said solid-state imaging device.

4. An apparatus or device according to claim 1 or 2, wherein said light source unit includes an aperture device which varies an opening area in accordance with a level of said light control signal.

5. An apparatus or device according to any one of claims 1 or 2, wherein said light control signal generating means includes a luminance signal generating means for generating a luminance signal from the output of said solid-state imaging device, an integration device for integrating said luminance signal through a predetermined period, and a divider for dividing an output of said integration device by said correction signal.

6. An apparatus or a device according to claim 5, wherein said light control signal generating means includes means for controlling opening and closing periods of a gate which controls a period of input of said luminance signal to said integration device.

7. An apparatus or device according to claim 1 or 2, wherein said level judging means includes a comparator which compares outputs from a plurality of said pixels located to correspond to an outside diameter of said image guide with a predetermined level which is slightly higher than a dark current level.

8. An apparatus or device according to claim 3, wherein said comparator is constituted by a digital comparator.

9. An apparatus or device according to claim 1 or 2, wherein said correction signal generating means includes a comparator for comparing outputs from pixels in a longitudinal or transverse row on said solid-state imaging device, an integration device integrating outputs from said comparator, and a sample hold circuit for sample-holding an output from said integration device.

10. An apparatus or device according to claim 9, wherein said light control signal generating means includes a luminance signal generating means for generating a luminance signal from the output of said solid-state imaging device, an integration device for integrating said luminance signal through a predetermined period, and a divider for dividing the output of said integration device by said correction signal.

11. An apparatus or a device according to claim 10, wherein said light control signal generating means includes means for controlling the opening and closing periods of a gate which controls the period of input of said luminance signal to said integration device.

12. An apparatus or device according to claim 1 or 2, wherein said correction signal generating means includes a plurality of correction voltage generating means for generating voltages corresponding to different area sizes of said image guide, and a selection means for selecting one from said plurality of voltages in accordance with a result of the determination excused by said level judging means.

13. An apparatus or device according to claim 12, wherein a single pixel is provided for each of a plurality of different imaging area sizes provided by different image guides.

14. An apparatus or device according to claim 12, wherein a plurality of pixels are provided for each of the different area sizes provided by different image guides.

15. An apparatus or device according to claim 12, wherein said selection means has an irreversible unidirectional switching characteristic for switching the correction voltage from one which corresponds to a smaller imaging area of the guide to one which corresponds to a larger imaging area of the image guide.

* * * * *